111111111111111111111111

US011517716B2

(12) United States Patent
Nguyen et al.

(10) Patent No.: US 11,517,716 B2
(45) Date of Patent: Dec. 6, 2022

(54) PULLER WIRE T-BAR FOR MEDICAL CATHETER

(71) Applicant: Biosense Webster (Israel) Ltd., Yokneam (IL)

(72) Inventors: Thanh Nguyen, El Monte, CA (US); Anand Rao, Tustin, CA (US); Joy Baybay, Irwindale, CA (US); Keshava Datta, Chino Hills, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 225 days.

(21) Appl. No.: 16/708,170

(22) Filed: Dec. 9, 2019

(65) Prior Publication Data

US 2020/0206466 A1 Jul. 2, 2020

Related U.S. Application Data

(60) Provisional application No. 62/786,401, filed on Dec. 29, 2018.

(51) Int. Cl.
*A61M 25/01* (2006.01)
*A61M 25/00* (2006.01)
(Continued)

(52) U.S. Cl.
CPC ..... *A61M 25/0147* (2013.01); *A61B 18/1492* (2013.01); *A61L 29/06* (2013.01);
(Continued)

(58) Field of Classification Search
CPC ........ A61M 25/0147; A61M 2025/015; A61B 18/1492; A61B 2017/00327; A61B 2017/00323; A61L 29/06
See application file for complete search history.

(56) References Cited

U.S. PATENT DOCUMENTS 4,960,134 A * 10/1990 Webster, Jr. ...... A61M 25/0147
607/116
RE34,502 E * 1/1994 Webster, Jr. ...... A61M 25/0147
607/125
(Continued)

FOREIGN PATENT DOCUMENTS

EP 0 900 575 A1 3/1999
EP 2 172 241 A2 4/2010

OTHER PUBLICATIONS

Communication pursuant to Artilce 94(3) EPC dated Feb. 1, 2022 issued in European Patent Application No.19219998.
(Continued)

*Primary Examiner* — Emily L Schmidt
*Assistant Examiner* — Adam J. Cermak
(74) *Attorney, Agent, or Firm* — Troutman Pepper Hamilton Sanders LLP

(57) ABSTRACT

A medical probe includes a generally tubular member with a tip portion coupled to the tubular member. A puller wire is disposed in the tubular member and configured for movement along the longitudinal axis to bend the tip portion with respect to the longitudinal axis. An anchor is disposed within the tubular member and connected to the puller wire such that the anchor has a t-bar. The t-bar includes a generally transverse extension and a ferrule connected to the puller wire. The t-bar has a polymeric member disposed on the generally transverse extension to increase a strength of the anchor with respect to forces applied to the puller wire to deflect the tip of the medical probe.

9 Claims, 7 Drawing Sheets

(51) Int. Cl.
  *A61B 18/14* (2006.01)
  *A61L 29/06* (2006.01)
  *A61B 18/00* (2006.01)

(52) U.S. Cl.
  CPC . *A61M 25/005* (2013.01); *A61B 2018/00577* (2013.01); *A61B 2018/1407* (2013.01); *A61B 2018/1467* (2013.01); *A61M 2025/015* (2013.01)

(56) References Cited

U.S. PATENT DOCUMENTS

| | | | | | |
|---|---|---|---|---|---|
| 5,562,619 | A | * | 10/1996 | Mirarchi | A61B 17/221 604/264 |
| 5,685,878 | A | * | 11/1997 | Falwell | A61B 18/1492 600/372 |
| 5,827,278 | A | * | 10/1998 | Webster, Jr. | A61B 18/1492 606/41 |
| 5,857,997 | A | * | 1/1999 | Cimino | A61M 25/0136 604/95.01 |
| 6,171,277 | B1 | * | 1/2001 | Ponzi | A61B 18/1492 604/22 |
| 6,298,257 | B1 | * | 10/2001 | Hall | A61B 5/06 600/407 |
| 6,371,955 | B1 | * | 4/2002 | Fuimaono | A61B 18/1492 606/29 |
| 6,374,476 | B1 | * | 4/2002 | Ponzi | A61B 18/1492 29/447 |
| 6,662,034 | B2 | * | 12/2003 | Segner | A61M 25/01 600/373 |
| 6,980,843 | B2 | * | 12/2005 | Eng | A61B 34/73 600/374 |
| 7,377,906 | B2 | * | 5/2008 | Selkee | A61M 25/0136 604/95.04 |
| 7,553,305 | B2 | * | 6/2009 | Honebrink | A61M 25/0147 604/264 |
| 7,678,104 | B2 | * | 3/2010 | Keidar | A61B 8/12 606/27 |
| 9,662,473 | B2 | * | 5/2017 | McDaniel | A61M 25/0147 |
| 9,849,268 | B2 | * | 12/2017 | Jimenez | A61M 25/0147 |
| 10,493,238 | B2 | * | 12/2019 | Selkee | A61M 25/0147 |
| 10,898,096 | B2 | * | 1/2021 | Chmielewski | A61M 39/14 |
| 2003/0208252 | A1 | * | 11/2003 | O' Boyle | A61B 18/1492 607/122 |
| 2009/0209950 | A1 | * | 8/2009 | Starksen | A61B 5/0215 606/21 |
| 2010/0168676 | A1 | * | 7/2010 | Datta | A61B 18/1492 604/171 |
| 2011/0282344 | A1 | * | 11/2011 | Whayne | A61B 18/082 606/49 |
| 2014/0221920 | A1 | * | 8/2014 | Jimenez | A61M 25/0147 604/95.04 |
| 2016/0143588 | A1 | * | 5/2016 | Hoitink | A61B 5/6859 600/374 |
| 2016/0279386 | A1 | * | 9/2016 | Dale | A61M 25/0133 |
| 2016/0331933 | A1 | * | 11/2016 | Knutsen | A61M 25/0147 |
| 2018/0272108 | A1 | * | 9/2018 | Padilla | A61M 25/005 |
| 2019/0351189 | A1 | * | 11/2019 | Hanenburg | A61M 25/0012 |

OTHER PUBLICATIONS

Extended European Search Report dated Jun. 26, 2020 issued in European Patent Application No. 19219998.

* cited by examiner

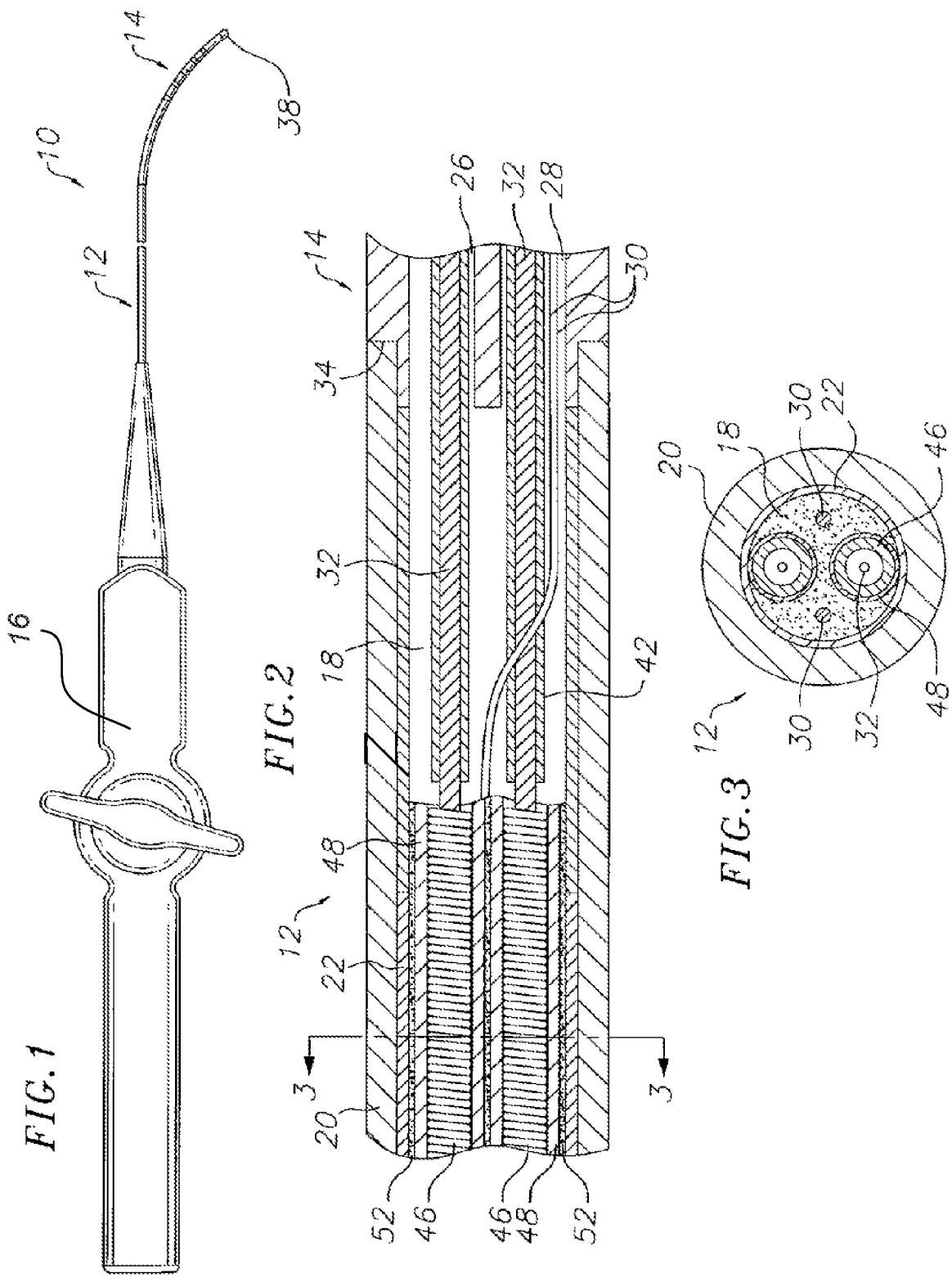

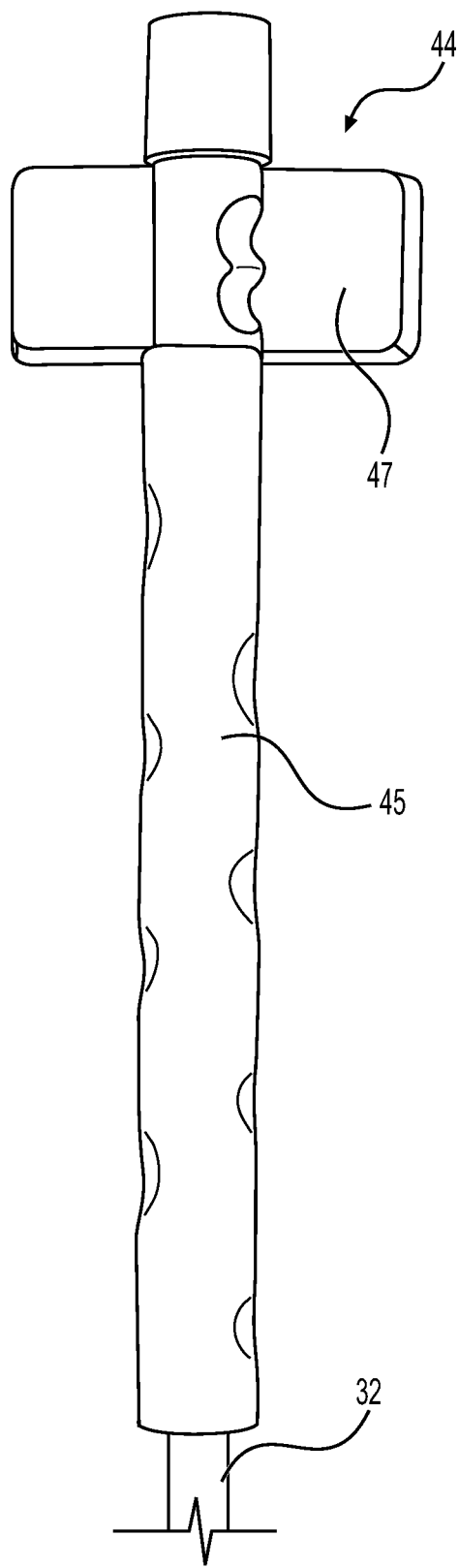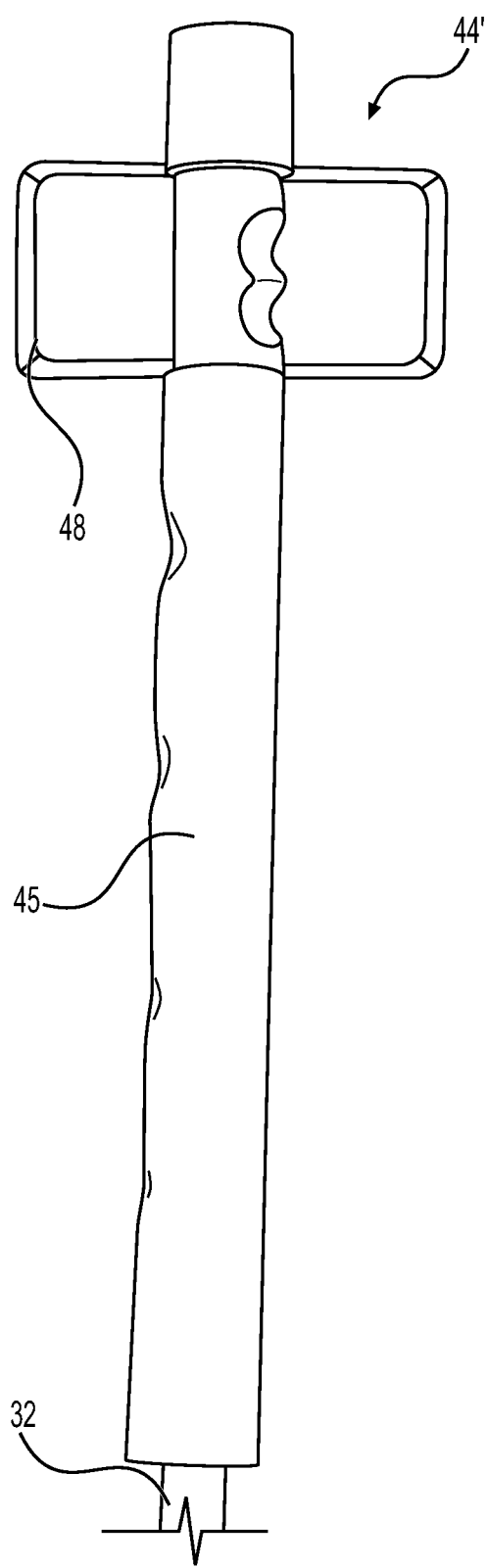
FIG. 10A
(PRIOR ART)
FIG. 10B

PULLER WIRE T-BAR FOR MEDICAL CATHETER

FIELD

The subject matter disclosed herein relates to electrophysiologic catheters, particularly those capable of ablating cardiac tissue.

BACKGROUND

Ablation of cardiac tissue has been used to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters may be visualized using fluoroscopy.

SUMMARY OF THE DISCLOSURE

We have devised an end probe for use in a catheter such that the end probe is able to sustain greater pulling forces being applied to puller wires in such end probe. In one embodiment, we have devised a medical probe to include a generally tubular member that extends from a proximal portion to a distal portion. The tubular member includes a tip portion, a puller wire, and an anchor. The tubular member extends along a longitudinal axis from a proximal portion to a distal portion. The tip portion is coupled to the tubular member proximate the distal portion of the medical probe. The puller wire is disposed in the tubular member and configured for movement along the longitudinal axis to bend the tip portion with respect to the longitudinal axis. The anchor is disposed in the tubular member and connected to the puller wire. The anchor consists of a t-bar that includes a generally transverse extension and a ferrule connected to the puller wire. The t-bar includes a polymeric member disposed on the generally transverse extension.

The following features are also combinable with the end probe such as, for example, the polymeric member may include a viscoelastic material; the viscoelastic material may include polyurethane; the polymeric member may include a high strength monofilament; the polymeric member may include a high strength fiber; the high strength fiber may include an ultra-high molecular weight fiber; the t-bar may include a metallic member; the t-bar may include a composite material that can be a combination of viscoelastic material and a metal; the transverse extension may include two transverse members extending from a central body and the polymeric member may include a polyurethane sleeve disposed over each of the transverse members; the polyurethane sleeve may include a tubular member having a thickness of about 0.004 inches.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

FIG. 1 is a side view of an embodiment of the catheter of the invention.

FIG. 2 is a side cross-sectional view of the junction of the catheter body and probe tip section of an embodiment of the probe according to the invention.

FIG. 3 is a transverse cross-sectional view of the probe shown in FIG. 2 taken along line 3-3.

FIG. 10A shows a photograph of a prior version of the anchor used in FIG. 9A.

FIG. 10B shows a photograph of an embodiment of the invention used in FIG. 9A.

MODES OF CARRYING OUT THE INVENTION

Figure 4:
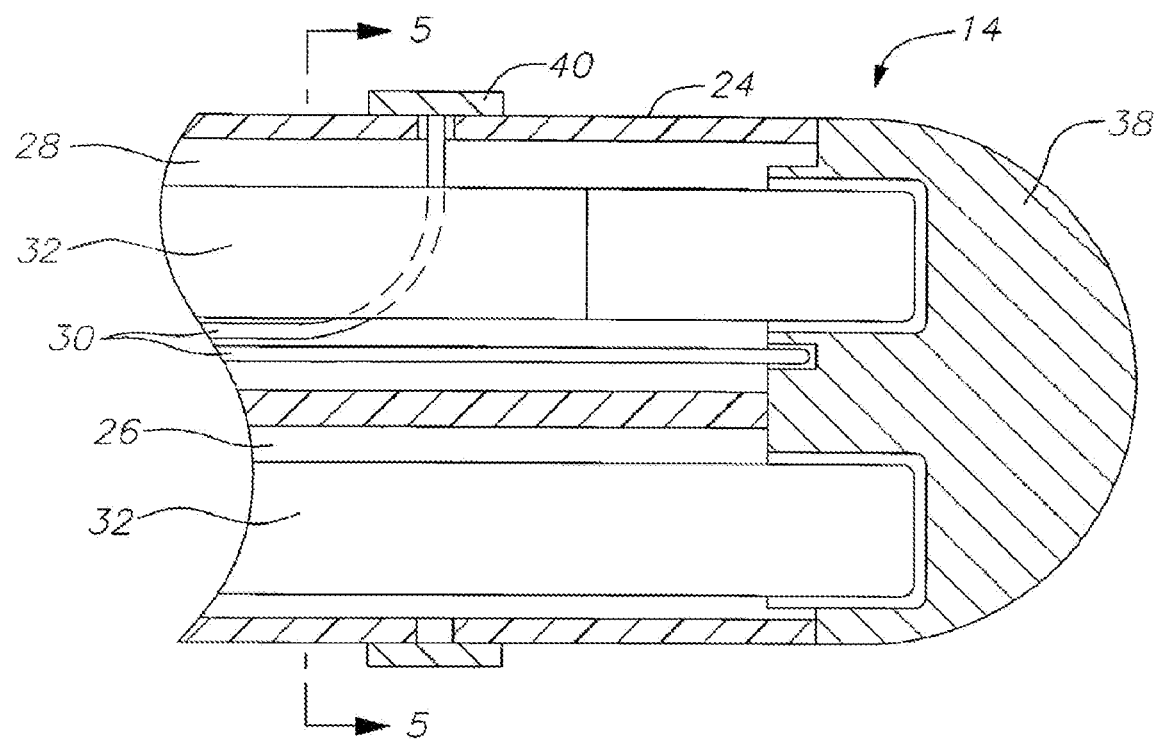
FIG. 4 is a side cross-sectional view of the distal end of the tip section shown in FIG. 2.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

In an embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX® (polyether block amide). The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical but is preferably no more than about 8 French. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch.

Figure 5:
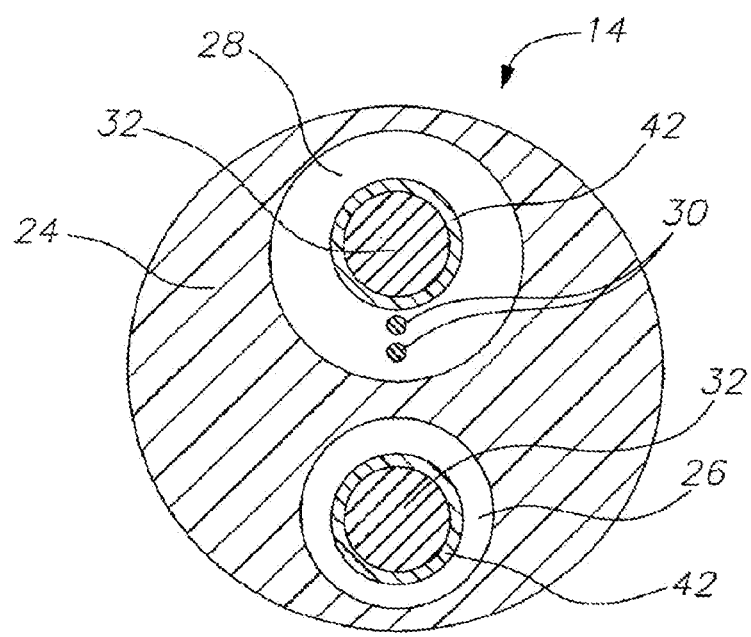
FIG. 5 is a transverse cross-sectional view of the tip section along line 5-5.
Figure 6:
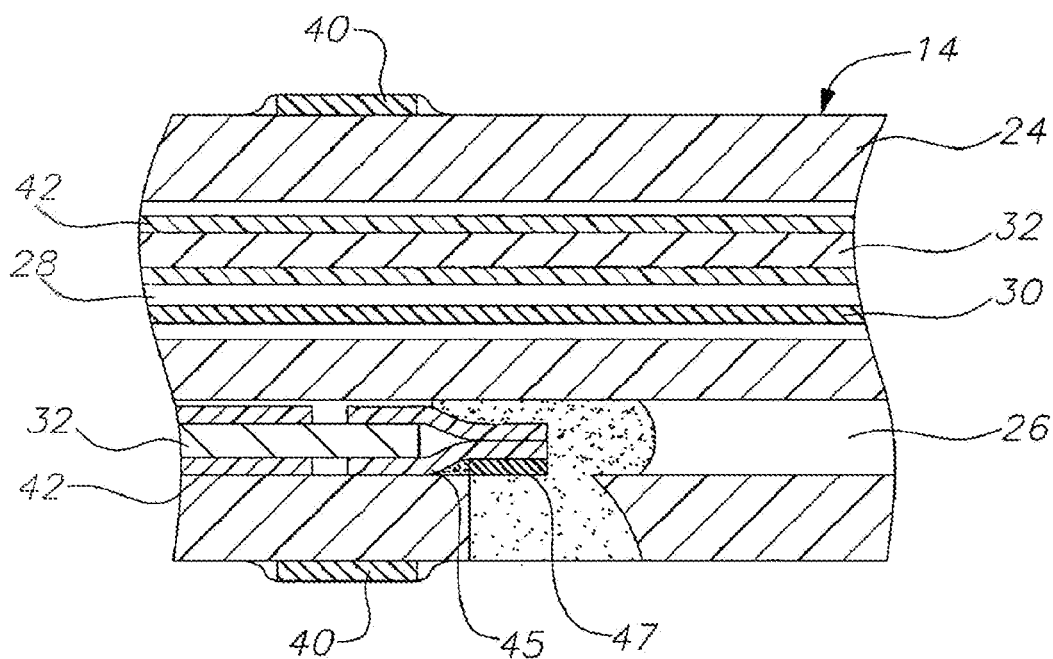
FIG. 6 is a transverse cross-sectional view of a catheter tip section where the puller wires are anchored to the side walls of the tip section.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 7 French, more preferably about 6½ French or less.

The off-axis lumens 26, 28 extend through diametrically opposed halves of the tip section 14. In an 8 French or 7 French diameter catheter, where the tip section is 6½ French, it is preferred that the off-axis lumens 26 and 28 have a diameter ranging from about 0.018 inch to about 0.025 inch, more preferably from about 0.018 inch to about 0.022 inch. By using two rather than three lumens along a single diameter, the present design retains the simplified construction of the unidirectional deflectable steerable catheter described in U.S. Pat. No. Re 34,502, which is incorporated herein by reference. However, it is understood that additional lumens may be provided in the tip section. As described in U.S. Pat. No. 6,171,277, the disclosure of which is incorporated herein by reference, the tip section 14 may contain four lumens, two of which have a greater diameter of about 0.035 inch and two of which have a lesser diameter of about 0.019 inch. Lead wires for the electrodes, thermocouple wires and/or electromagnetic sensor cable may extend through different lumen(s) from those through which each of puller wires extends. As such, the present invention may employ two or more lumens in the tip section 14.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast-drying glue, e.g. Super Glue. Thereafter a second glue joint is formed between the proximal ends of the stiffening tube 22 and outer wall 20 using a slower drying but stronger glue, e.g., polyurethane.

In the depicted embodiment, the distal end of the tip section 14 carries a tip electrode 38 (see FIGS. 1 and 4). Mounted along the length of the tip section 14 is a ring electrode 40 (see FIG. 4). The length of the ring electrode 40 is not critical but is preferably about 0.5 mm to about 3 mm. Additional ring electrodes can be provided if desired. If multiple ring electrodes are used, they are spaced apart in any fashion as desired so long as their edges do not touch.

As shown in FIGS. 2-5, the tip electrode 38 and ring electrode 40 are each connected to a separate lead wire 30. Each lead wire 30 extends through the second off-axis lumen 28 in the tip section 14 (FIG. 5), through the central lumen 18 in the catheter body 12 (FIG. 3) and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to the ring electrode 40 is preferably accomplished by first making a small hole through the tubing 24. Such a hole can be created, for example, by inserting a needle through the tubing 24 and heating the needle sufficiently to form a permanent hole. The lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

As also shown in FIGS. 2-5, two puller wires 32 extend through the catheter 10. Each puller wire 32 extends from the control handle 16, through the central lumen 18 in the catheter body 12 (FIG. 3) and into one of the off-axis lumens 26 and 28 of the tip section 14 (FIG. 5). As described in more detail below, proximal movement of the proximal end of each puller wire 32 is predetermined limited within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of low friction polymer or the like. Each puller wire 32 has a diameter preferably ranging from about 0.006 inch to about 0.010 inch. Preferably both of the puller wires 32 have the same diameter.

Each puller wire 32 is anchored near the distal end of the tip section 14. In the embodiment depicted in FIG. 4, the puller wires 32 are both anchored to the tip electrode 38 by a welding or the like.

Figure 7:
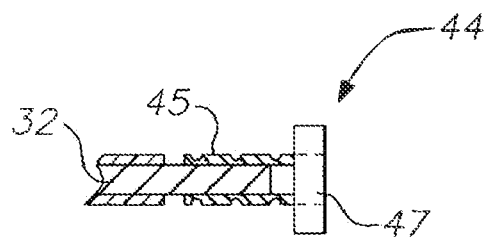
FIG. 7 is a longitudinal cross-sectional view of a preferred puller wire T-bar anchor.
Figure 8:
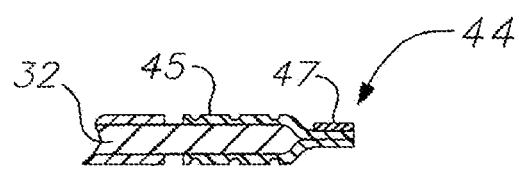
FIG. 8 is a longitudinal cross-sectional view of the puller wire T-bar anchor of FIG. 7 rotated about 90 degrees to show the cross-piece on end.

Alternatively, the puller wire 32 in the first off-axis lumen 26 can be anchored to the side wall of the tip section 14. As shown in FIGS. 7 to 9, the puller wire 32 is preferably attached by means of an anchor 44 fixedly attached to the distal end of the puller wire 32. The anchor 44 is formed by a metal tube 45, e.g., a ferrule connected to the puller wire stock, that is fixedly attached, e.g. by crimping or welding, to the distal end of the puller wire 32. The tube has a section that extends a short distance beyond the distal end of the puller wire 32. A cross-piece 47 made of a small section of a flat, stainless steel ribbon or the like is soldered or welded in a transverse arrangement to the distal end of the metal tube. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is wider than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. Additional lumens can be provided to permit passage of the lead wires, irrigation fluid or other items (not shown) to pass to the distal end. Other means for anchoring the puller wires 32 in the tip section 14 would be recognized by those skilled in the art and are included within the scope of the invention.

Referring back to FIGS. 1 and 2, the catheter 10 further comprises two compression coils 46, each in surrounding relation to a corresponding puller wire 32. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. The non-conductive sheath 48 made of thin-walled polyimide tubing is presently preferred. In the preferred embodiment, the compression coil 46 and puller wire 30 are disposed in lumen 18 with off-axis lumens 26, 28 utilized for passage of electrical wires or as an irrigation flow path.

As shown in FIG. 2, at the distal end of the catheter body, the two compression coils 46 are positioned in diametric opposition within the stiffening tube 22 so that they can be aligned with the two off-axis lumens 26, 28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

Still referring to FIG. 2, the distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26, 28 of the tip section 14 and are anchored at their distal ends to the proximal end of the tip section 14 by a glue joint. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46.

As best shown in FIGS. 2 and 5, within the off-axis lumens 26, 28, each puller wire 32 is surrounded by a plastic sheath 42, preferably made of a suitable low friction polymer. The plastic sheaths 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of the puller wires 32 relative to the catheter body 12, which results in deflection of the tip section 14, is accomplished by manipulation of the control handle 16. A suitable bidirectional control handle for use in the present invention is illustrated in FIGS. 9-24 of U.S. Pat. No. 7,377,906, which prior patent is incorporated by reference in its entirety herein this application.

Figure 9A:
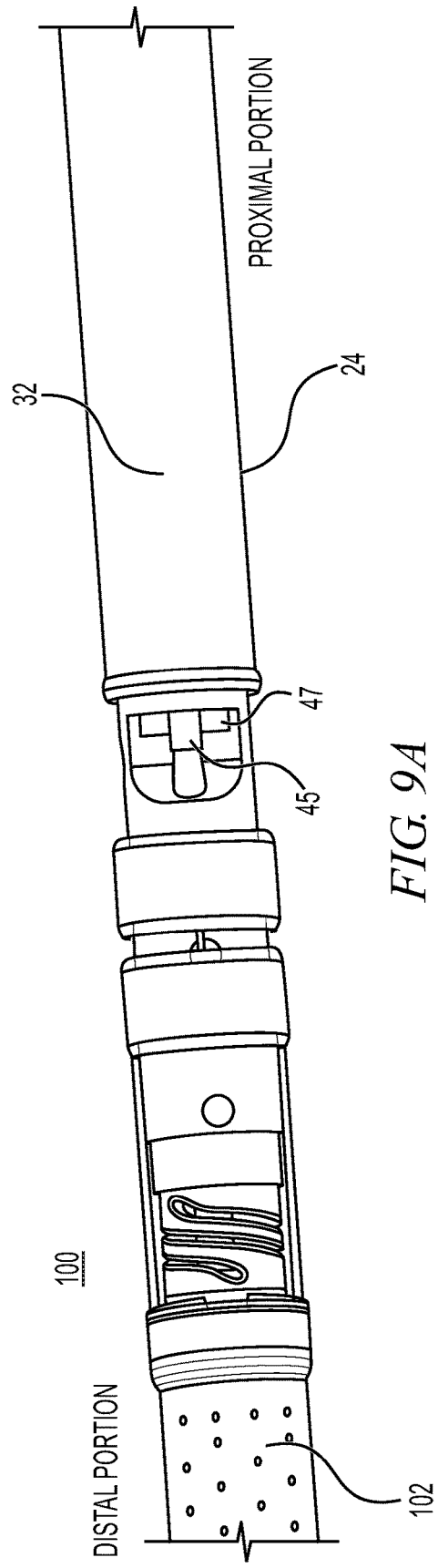
FIG. 9A is a side view of one embodiment of a medical probe.
Figure 9B:
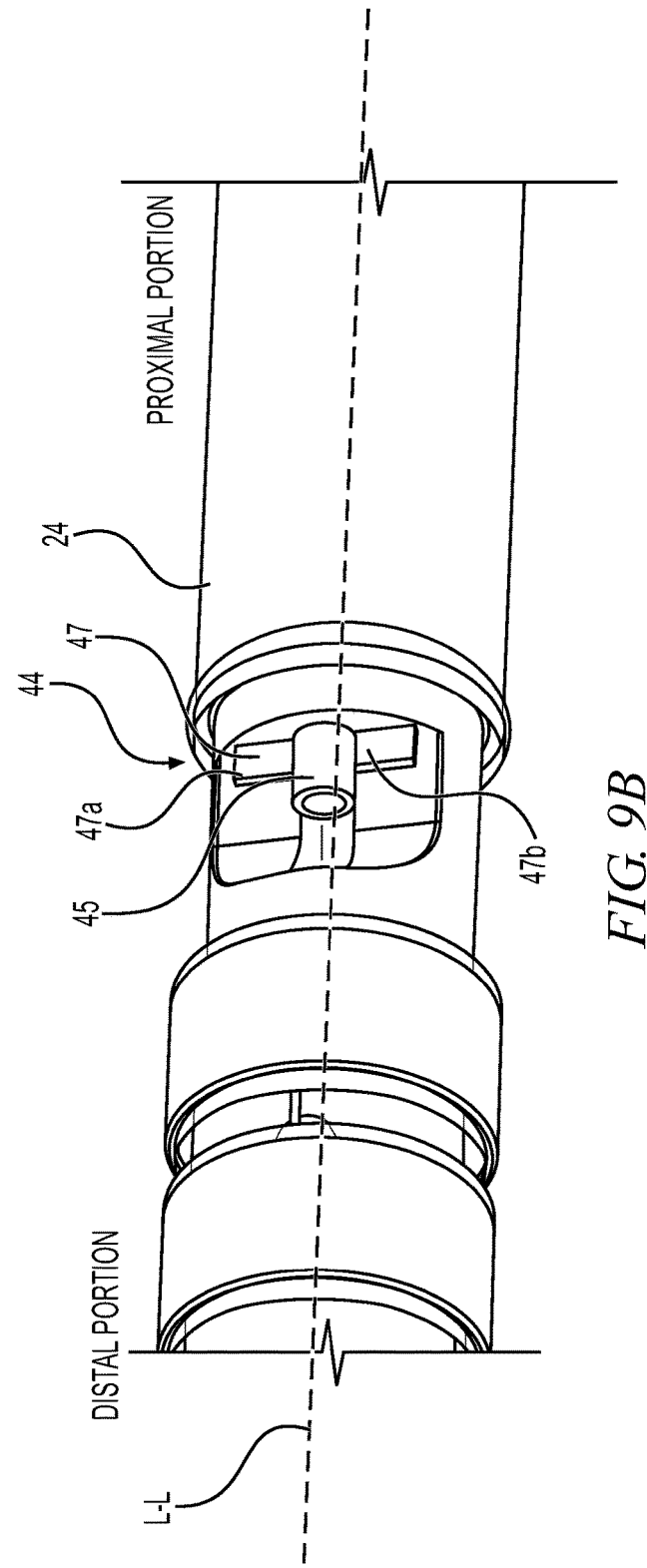
FIG. 9B is a perspective side view of an enlarged portion of the medical probe of FIG. 9A.
Figure 11:
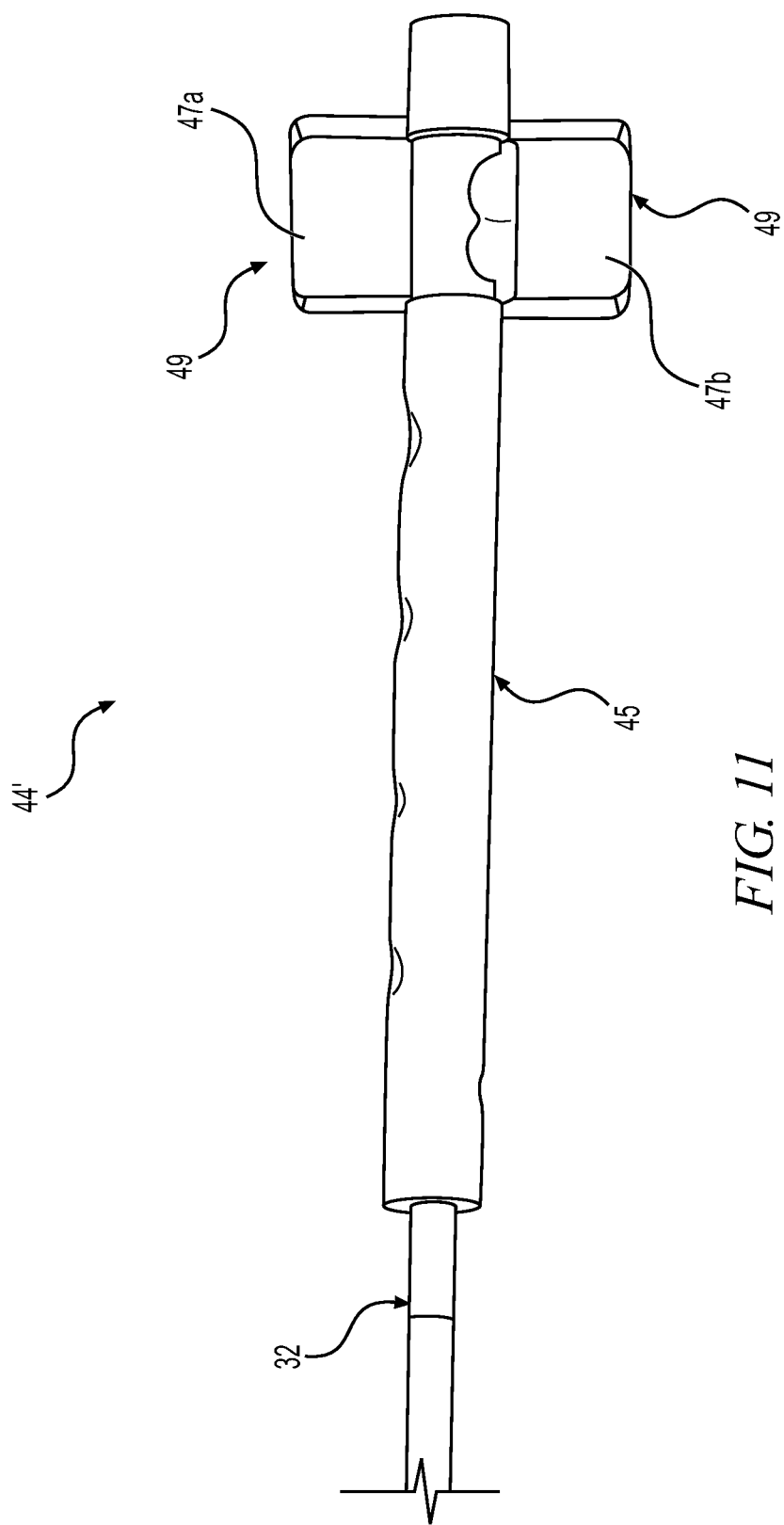
FIG. 11 shows another view of the anchor of FIG. 10B.
Figure 12:
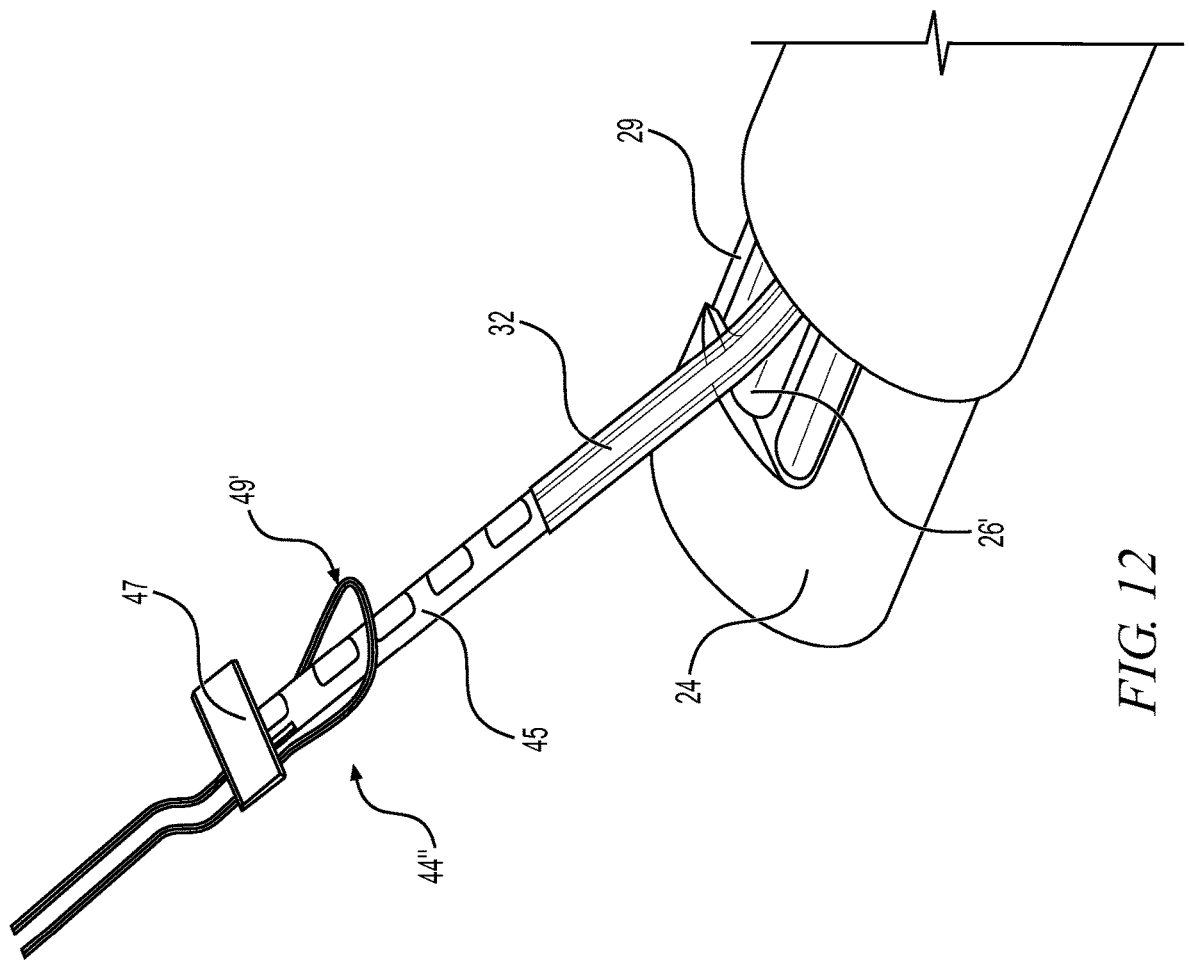
FIG. 12 illustrates a perspective view of yet another embodiment of the polymeric member utilized to improve the ability of the anchor to sustain greater pulling force as applied to the puller wire.

Referring to FIGS. 9A and 9B, we have devised a configuration of the anchor 44 to allow greater pulling force to be applied to the pull wires. In this configuration, the medical probe 100 includes at least a generally tubular member 24 that extends from a proximal portion to a distal portion. The tubular member 24 includes a tip portion 102, a puller wire 32, and an anchor 44. The tubular member 24 extends along a longitudinal axis L-L from a proximal portion to a distal portion. The tip portion 102 is coupled to the tubular member 24 proximate the distal portion of the medical probe 100. The puller wire 32 is disposed in the tubular member 24 and configured for movement along the longitudinal axis L-L to bend the tip portion 102 with respect to the longitudinal axis L-L. The anchor 44 is disposed in the tubular member 24 and connected to the puller wire 32 via a t-bar 47. The t-bar 47 includes a generally transverse extension in the form of wings 47a and 47b and a ferrule 45 connected to the puller wire 32. This configuration of the anchor 44 can be seen in FIG. 10A.

We have improved the anchor 44 of FIG. 10A by virtue of a polymeric member 48 disposed on the generally transverse extension 47 of the t-bar to arrive at a new anchor configuration 44', shown here in FIG. 10B. As shown separately in FIG. 11, anchor 44' includes the ferrule 45 which is fixedly connected to the pull wire 32 and two generally transverse extensions 47a and 47b with a polymeric member 49 (illustrated as an amber material) disposed over each of the transverse wings 47a and 47b.

In one embodiment, the polymeric member 49 may include a viscoelastic material such as, for example, polyurethane. By implementing the polymeric member 49, the anchor 44' allows a greater pulling force to be sustained by the pull wire 32. As shown in the Table, the average pull force is increased by about 36% for the sample size of a medical probe using anchor 44 versus that using anchor 44'.

| MEDICAL PROBE WITH ANCHOR 44 | | MEDICAL PROBE WITH NEW ANCHOR 44' | |
|---|---|---|---|
| Sample # | Full force (lbf) | Sample # | Full force (lbf) |
| 1-A | 9.8 | 1-A | 12.8 |
| 1-B | 10.5 | 1-B | 12.6 |
| 2-A | 10.3 | 2-A | 12.8 |
| 2-B | 9.1 | 2-B | 13.2 |
| 3-A | 9.4 | 3-A | 12.3 |
| 3-B | 8.8 | 3-B | 12.9 |
| 4-A | 10.2 | 4-A | 12.6 |
| 4-B | 9.0 | 4-B | 13.0 |
| 5-A | 9.6 | 5-A | 13.8 |
| 5-B | 8.7 | 5-B | 13.2 |
| Average | 9.5 | Average | 12.9 |
| Stdev | 0.6 | Stdev | 0.4 |
| Min | 8.7 | Min | 12.2 |
| Max | 10.5 | Max | 13.8 |

In an alternate embodiment of anchor 44', the polymeric member 49 may include a high strength monofilament or a high strength fiber 49' such as, for example, an ultra-high molecular weight fiber for anchor 44". The monofilament or fiber 49' of anchor 44" is configured to be wrapped at least once around central body 45 and contiguous to the extensions 47a and 47b with free ends of the fiber 49' that extend for a predetermined distance from the t-bar 47 into the remaining lumen sectional portion 26' of the puller wire lumen 26 toward the distal direction for about 0.100 inches (or about 2.5 mm). Additionally, polymeric member 49' is then secured by glue or the like within remaining lumen section 26'. Tensile forces from anchor 45 are thereby distributed within slot 29 formed in the tubular member 24 as well as into lumen section 26'. The t-bar 47 may include a metallic member such as a biocompatible metal or alloys of such metals including for example, stainless steel. Alternatively, the t-bar 47 may include a composite material of metal and polymer or a polymer alone. While the t-bar 47 is shown with two generally symmetrical extensions 47a and 47b extending from a central body 45, the t-bar 47 may include other forms of geometrical structure as extensions as well as a single rectilinear extension protruding from the central ferrule body 45.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

Any of the examples or embodiments described herein may include various other features in addition to or in lieu of those described above. The teachings, expressions, embodiments, examples, etc. described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A medical probe comprising:
   a generally tubular member extending along a longitudinal axis from a proximal portion to a distal portion;
   a tip portion coupled to the tubular member proximate the distal portion of the medical probe;
   a puller wire disposed in the tubular member and configured for movement along the longitudinal axis to bend the tip portion with respect to the longitudinal axis; and
   an anchor disposed in the tubular member and connected to the puller wire, the anchor having a t-bar that includes a generally transverse extension and a ferrule connected to the puller wire, the t-bar being fixedly attached to the tubular member with a glue, the t-bar being coated with a polyurethane sleeve disposed on the generally transverse extension.

2. The medical probe of claim 1, wherein the polyurethane sleeve comprises a viscoelastic material.

3. The medical probe of claim 2, wherein the viscoelastic material comprises polyurethane.

4. The medical probe of claim 1, wherein the t-bar comprises a metallic member.

5. The medical probe of claim 1, wherein the t-bar comprises a composite material.

6. The medical probe of claim 5, wherein the composite material comprises a combination of viscoelastic material and a metal.

7. The medical probe of claim 1, wherein the transverse extension comprises two transverse members extending from a central body and the polyurethane sleeve is disposed over each of the transverse members.

8. The medical probe of claim 7, wherein the polyurethane sleeve comprises a tubular member having a thickness of about 0.004 inches.

9. The medical probe of claim 1, wherein the wire comprises a stainless-steel wire.

* * * * *